United States Patent
Wismer et al.

[11] Patent Number: 6,013,846
[45] Date of Patent: Jan. 11, 2000

[54] AZEOTROPE OF HF AND 1233ZD

[75] Inventors: John A. Wismer, Lower Makefield; Michael S. Bolmer, Lower Providence; Bin Chen, Tredyffrin, all of Pa.

[73] Assignee: Elf Atochem North America, Inc., Philadelphia, Pa.

[21] Appl. No.: 09/035,696

[22] Filed: Mar. 5, 1998

[51] Int. Cl.[7] ........................................... C07C 17/38
[52] U.S. Cl. .................. 570/180; 570/164; 570/165; 570/166; 570/167; 570/168; 570/169; 570/177; 570/180
[58] Field of Search .................. 570/166, 167, 570/168, 169, 177, 180, 164, 165

[56] References Cited

U.S. PATENT DOCUMENTS

| | | | |
|---|---|---|---|
| 5,414,165 | 5/1995 | Nappa et al. | 570/169 |
| 5,545,774 | 8/1996 | Rao | 570/168 |
| 5,616,819 | 4/1997 | Boyce et al. | 570/167 |
| 5,710,352 | 1/1998 | Tung | 570/166 |
| 5,763,706 | 6/1998 | Tung et al. | 570/167 |
| 5,874,658 | 2/1999 | Belter | 570/180 |

*Primary Examiner*—James O. Wilson

[57] ABSTRACT

An azeotrope containing HF and 1233zd is provided, as are methods for separating this azeotrope from mixtures of HF and 1233zd which are HF-rich or 1233zd-rich and methods for making use of the azeotrope and separation methods to improve processes for preparing 1233zd, an intermediate used in the preparation of 245fa. 245fa is a known foam blowing agent and refrigerant.

11 Claims, No Drawings

AZEOTROPE OF HF AND 1233ZD

BACKGROUND OF THE INVENTION

This invention relates to an azeotrope containing hydrogen fluoride (referred to hereinafter as "HF") and 1,1,1-trifluoro-3-chloro-2-propene (referred to hereinafter as "1233zd"), to methods for separating this azeotrope from mixtures of HF and 1233zd which are HF-rich or 1233zd-rich, and to methods for making use of the azeotrope and separation methods to improve processes for preparing 1233zd, a known intermediate for the preparation of 1,1,1,3,3-pentafluoropropane (referred to hereinafter as "245fa"), as taught, for example in U.S. Pat. No. 5,616,189. 245fa is known to have utility as a foam blowing agent and refrigerant.

A number of processes in the prior art make 245fa by first making the 1233zd intermediate. For example, 1233zd can be made by fluorination of 1,1,1,3,3-pentachloropropane ("240fa") or fluorination of 1,1,3,3-tetrachloro-2-propene (referred to hereinafter as "1230za"). The 1230za is of special interest as a starting material since it has been shown to fluorinate readily in the liquid phase without a catalyst, as taught in copending U.S. Pat. application Ser. No. 09/013,839, filed Jan. 27, 1998 (now U.S. Pat. No. 5,877,359). The 1233zd intermediate can then be fluorinated directly or through other intermediates to make 245fa. One of the problems associated with the 1233zd intermediate, however, is that it has the same boiling point (20° C.) as HF, posing a problem of how to recover sufficient HF to make the process economical.

Heterogeneously catalyzed gas phase processes can also be used for fluorinating 240fa or 1230za to 1233zd, as disclosed, for example, in Application WO 97/24307 and copending U.S. Pat. application Ser. No. 08/980,746, filed Dec. 1, 1997, (now U.S. Pat. No. 5,811,603). A major problem associated with gas phase reactions, however, is that the precursor compounds have high boiling points (179° C. for 240fa and 149° C. for 1230za) and low thermal stability at elevated temperatures. Furthermore, their decomposition can be catalyzed in the liquid phase by acids such as HF, which is a reactor feed. It would thus be useful to develop a process which could be used to lower the volatility of the organic feed and thereby avoid its thermal decomposition.

In this application "distillation column" and "rectification column" are sometimes used interchangeably. Actually, however, a rectification column is a specific type of distillation column. In most distillation columns the material to be distilled is fed to the middle of the column; below the feed point is called the stripping section and above the feed point is called the rectification section. Reference is made herein to a rectification column when the material to be distilled is instead fed to the bottom of the "distillation column."

BRIEF SUMMARY OF THE INVENTION

Herein provided, among other things, are an azeotropic composition consisting essentially of HF and 1233zd; a method for separating HF from a mixture containing HF and 1233zd (and, optionally, hydrogen chloride or "HCl") which is rich in HF relative to the azeotropic composition, which method comprises treating said mixture in a distillation (rectification) column to obtain a distillate containing the azeotropic composition (and the HCl, if any) and a bottom product of relatively pure HF; a method for producing 1233zd which comprises (a) contacting 1230za and HF in the liquid phase in a feed ratio of HF to 1230za which is at least equal to the sum of the stoichiometric ratio of the feeds (3.0) and the azeotropic ratio of HF to 1233zd to create a reaction mixture containing HF, 1233zd, and HCl, which mixture is rich in HF relative to the azeotropic composition of HF and 1233zd and (b) treating the mixture from (a) in a distillation (rectification) column to obtain a distillate containing HCl and the azeotropic composition of HF and 1233zd and a bottom product of relatively pure HF, which bottom product is preferably recycled for use as part of the HF feed; a method for separating 1233zd from a mixture containing HF and 1233zd (and, optionally, 245fa and/or HCl), which mixture is rich in 1233zd relative to the azeotropic composition, which method comprises treating said mixture in a distillation column to obtain a distillate containing the azeotropic composition of HF and 1233zd (and the HCl, if any) and a bottom product of relatively pure 1233zd (and a predominant amount of the 245fa, if any); and a method for producing 1233zd which comprises (a) contacting HF and an organic feed selected from 1230za and 240fa in the gas phase in a feed ratio of HF to organic feed which is at least equal to the stoichiometric ratio of the feeds but less than the sum of the stoichiometric ratio of the feeds and the azeotropic ratio of HF to 1233zd to create a reaction mixture containing HF, 1233zd, and HCl (and optionally, some 245fa), which mixture is rich in 1233zd relative to the azeotropic composition of HF and 1233zd, (b) treating the mixture from (a) in a distillation column to obtain a distillate containing HCl and the azeotropic composition of HF and 1233zd and a bottom product of relative pure 1233zd (and a predominant amount of any 245fa) and (c) recycling the bottom product for use as part of the organic feed. Each of the foregoing processes is preferably operated continuously.

DETAILED DESCRIPTION

An azeotrope of HF and 1233zd has now been found which can be used to remove an HF/1233zd azeotrope from a system which is rich in HF or to remove an HF/1233zd azeotrope from a pure 1233zd stream, which separation methods are particularly useful to solve the problems discussed above which are associated with liquid and gas phase processes for making 1233zd.

HF and 1233zd have been found to have a low boiling (high volatility) azeotrope. This azeotropic composition (at 20° C. and 50° C.) is shown below in Table 1:

TABLE 1

| Temperature (° C.) | Pressure (psia) | Mols HF/Mol 1233zd in Azeotrope |
| --- | --- | --- |
| 20 | 29 | 2.90 |
| 50 | 77 | 2.33 |

Application of the use of a rectification column to separate an HF/1233zd azeotrope from a stream which is rich in HF is particularly useful in relation to the liquid phase processes for producing 1233zd from 1230za in an HF rich medium, since avoidance of oligomer formation requires the use HF/1230za feed ratios which are in excess of the sum of the stoichiometric ratio (3.0) and the (HF/1233zd) azeotropic ratio, thus assuring that the resulting HF/1233zd/HCl reaction mixture will be HF-rich relative to the HF/1233zd azeotropic ratio. In practice this reaction mixture can be removed from the reactor as a gas and fed to the bottom of a rectification column, with the liquid bottoms containing the purified HF being recycled to the reactor. The distillate (HCl and HF/1233zd azeotrope) is removed overhead and may be treated by conventional means in a second distillation column to recover the HCl as overhead and the HF/1233zd as bottoms. Reactor temperatures between about 70° C. and 120° C. and rectification column pressures between about 130 psia and 275 psia are typically employed. For example, the process can be run at a reactor temperature of 70–85° C. and a rectification column pressure of 140 psia, using a minimum HF/1230za feed ratio of 5.4.

Application of the use of a distillation column to separate an HF/1233zd azeotrope from a stream which is rich in 1233zd is particularly useful in relation to the gas phase processes for producing 1233zd from 240fa or 1230za, since recycle of the 1233zd (boiling point of only 20° C.), and any 245fa which is formed (boiling point of about 14° C.), for use as part of the organic feed lowers the volatility of the organic feed and thereby helps to avoid its thermal decomposition. In order to generate the 1233zd-rich reaction mixture, HF/organic feed ratios are used which are in excess of the stoichiometric ratio but less than the sum of the stoichiometric ratio and the (HF/1233zd) azeotropic ratio.

The following are two examples of this embodiment wherein 1230za or 240fa is fluorinated with HF in the gas phase to produce a reaction mixture containing HCl, HF, 1233zd, and, optionally, 245fa, which reaction mixture is 1233zd-rich relative to the azeotropic ratio, the reaction mixture is distilled to obtain a distillate containing primarily the HF/1233zd azeotrope and HCl and a bottoms containing purified 1233zd and the predominant amount of any 245fa formed is recycled for use as part of the feed. In either case, the recycle stream generally contains a mol ratio of 1233zd/245fa recycle to the 1230za or 240fa precursor of between about 1 and 20, but preferably between about 3 and 8; the reactor temperature depends on the catalyst but is preferably in the range of about 150–200° C.; and the distillation column pressure is generally about 120–250 psia (preferably 150–225 psia):

A) Using 1230za as the feed, the system is operated so that the recycle stream contains about 3 mols of 1233zd and 0.8 mol of 245fa per mol of 1230za and the HF: 1230za mol ratio is about 5.4, about 3.4 being required for reaction to 1233zd and 245fa, with about 2 mols of HF being present in the reaction mixture so that the reaction mixture is rich in 1233zd relative to the azeotropic ratio. The reaction mixture effluent can be fed to the distillation column as a liquid, a gas, or a mixed phase. The distillation column removes HCl and 1233zd/HF azeotrope as overhead (for conventional separation as in the liquid phase system) and recycles 1233zd and 245fa in the ratios noted above.

B) Using 240fa as the feed, the system is operated so that the recycle stream contains about 5 mols of 1233zd and 0.8 mol of 245fa per mol of 240za and the HF:240za mol ratio is about 5.5, about 3.4 being required for reaction to 1233zd and 245fa, with about 2.1 mols of HF being present in the reaction mixture so that the reaction mixture is rich in 1233zd relative to the azeotropic ratio. The reaction mixture effluent can be fed to the distillation column as a liquid, a gas, or a mixed phase. The distillation column removes HCl and 1233zd/HF azeotrope as overhead (for conventional separation as in the liquid phase system) and recycles 1233zd and 245fa in the ratios noted above.

We claim:

1. An azeotropic composition consisting essentially of hydrogen fluoride and 1,1,1-trifluoro-3-chloro-2-propene.

2. A method for separating an azeotropic composition of hydrogen fluoride and 1,1,1-trifluoro-3-chloro-2-propene from a mixture including hydrogen fluoride and 1,1,1-trifluoro-3-chloro-2-propene, which mixture is rich in hydrogen fluoride relative to said azeotropic composition, which method comprises treating said mixture in a distillation column to obtain a distillate including said azeotropic composition and a bottom product including the balance of the hydrogen fluoride.

3. A method as in claim 2 wherein the mixture also includes hydrogen chloride and wherein said hydrogen chloride also comes over as part of said distillate.

4. A method as in claim 3 which further comprises treating the distillate in a second distillation column to obtain a second distillate including purified hydrogen chloride and a bottom product including the azeotropic composition of hydrogen fluoride and 1,1,1-trifluoro-3-chloro-2-propene.

5. A method for producing 1,1,1-trifluoro-3-chloro-2-propene which comprises (a) contacting 1,1,3,3-tetrachloro-2-propene and hydrogen fluoride in the liquid phase in a feed ratio of hydrogen fluoride to 1,1,3,3-tetrachloro-2-propene which is at least equal to the sum of the stoichiometric ratio of the feeds and the azeotropic ratio of hydrogen fluoride to 1,1,1-trifluoro-3-chloro-2-propene to create a reaction mixture including hydrogen fluoride, 1,1,1-trifluoro-3-chloro-2-propene, and hydrogen chloride which mixture is rich in hydrogen fluoride relative to the azeotropic composition of hydrogen fluoride and 1,1,1-trifluoro-3-chloro-2-propene; and (b) treating said mixture in a distillation column to obtain a distillate including hydrogen chloride and the azeotropic composition of hydrogen fluoride and 1,1,1-trifluoro-3-chloro-2-propene and a bottom product of purified hydrogen fluoride.

6. A method as in claim 5 wherein said bottom product is recycled for use as part of the hydrogen fluoride feed.

7. A method for separating an azeotropic composition of hydrogen fluoride and 1,1,1-trifluoro-3-chloro-2-propene from a mixture including hydrogen fluoride and 1,1,1-trifluoro-3-chloro-2-propene, which mixture is rich in 1,1,1-trifluoro-3-chloro-2-propene relative to said azeotropic composition, which method comprises treating said mixture in a distillation column to obtain a distillate including said azeotropic composition and a bottom product including the balance of the 1,1,1-trifluoro-3-chloro-2-propene.

8. A method as in claim 7 wherein the mixture also includes 1,1,1,3,3-pentafluoropropane and wherein said 1,1,1,3,3-pentafluoropropane also forms part of the bottom product.

9. A method as in claim 8 wherein the mixture also includes HCl and wherein said HCl also comes over as part of said distillate.

10. A method as in claim 9 which further comprises treating the distillate in a second distillation column to obtain a second distillate including purified hydrogen chloride.

11. A method for producing 1,1,1-trifluoro-3-chloro-2-propene which comprises (a) contacting hydrogen fluoride and an organic feed selected from 1,1,3,3-tetrachloro-2-propene and 1,1,1,3,3-pentachloropropane in the gas phase in a feed ratio of hydrogen fluoride to organic feed which is at least equal to the stoichiometric ratio of the feeds but less than the sum of the stoichiometric ratio of the feeds and the azeotropic ratio of hydrogen fluoride to 1,1,1-trifluoro-3-chloro-2-propene to create a reaction mixture including hydrogen fluoride, 1,1,1-trifluoro-3-chloro-2-propene, and hydrogen chloride which mixture is rich in 1,1,1-trifluoro-3-chloro-2-propene relative to the azeotropic composition of hydrogen fluoride and 1,1,1-trifluoro-3-chloro-2-propene; (b) treating said mixture in a distillation column to obtain a distillate including hydrogen chloride and said azeotropic composition and a bottom product of purified 1,1,1-trifluoro-3-chloro-2-propene; and (c) recycling said bottom product for use as part of the organic feed.

* * * * *